United States Patent [19]

Hauser et al.

[11] Patent Number: 4,543,428

[45] Date of Patent: Sep. 24, 1985

[54] PRODUCTION OF A HEXAHYDRONAPHTHALENONE COMPOUND

[75] Inventors: Frank M. Hauser, Portland; Dipakranjan Mal, Beaverton, both of Oreg.

[73] Assignee: Oregon Graduate Center for Study & Research, Beaverton, Oreg.

[21] Appl. No.: 618,838

[22] Filed: Jun. 8, 1984

Related U.S. Application Data

[62] Division of Ser. No. 474,491, Mar. 11, 1983, Pat. No. 4,481,143.

[51] Int. Cl.$^4$ ............................................. C07C 49/553
[52] U.S. Cl. .................................... 568/345; 568/347; 568/374; 560/256; 549/399

[58] Field of Search ............... 568/345, 347, 374, 364; 560/256; 260/544 L; 549/399

[56] References Cited

U.S. PATENT DOCUMENTS 3,072,709  1/1963  Saucy .................................. 568/374

OTHER PUBLICATIONS

Hauser et al., J. American Chemical Society, vol. 105, pp. 5688–5689, (1983).

*Primary Examiner*—James H. Reamer
*Attorney, Agent, or Firm*—Kolisch, Hartwell and Dickinson

[57] ABSTRACT

The compound 6-acetyl-4a,5,6,7,8,8a-hexahydro-1(4H)-naphthalenone, and preparation thereof beginning from 2-(2-hydroxyethyl)bicyclo[2.2.2]oct-5-ene.

2 Claims, 1 Drawing Figure

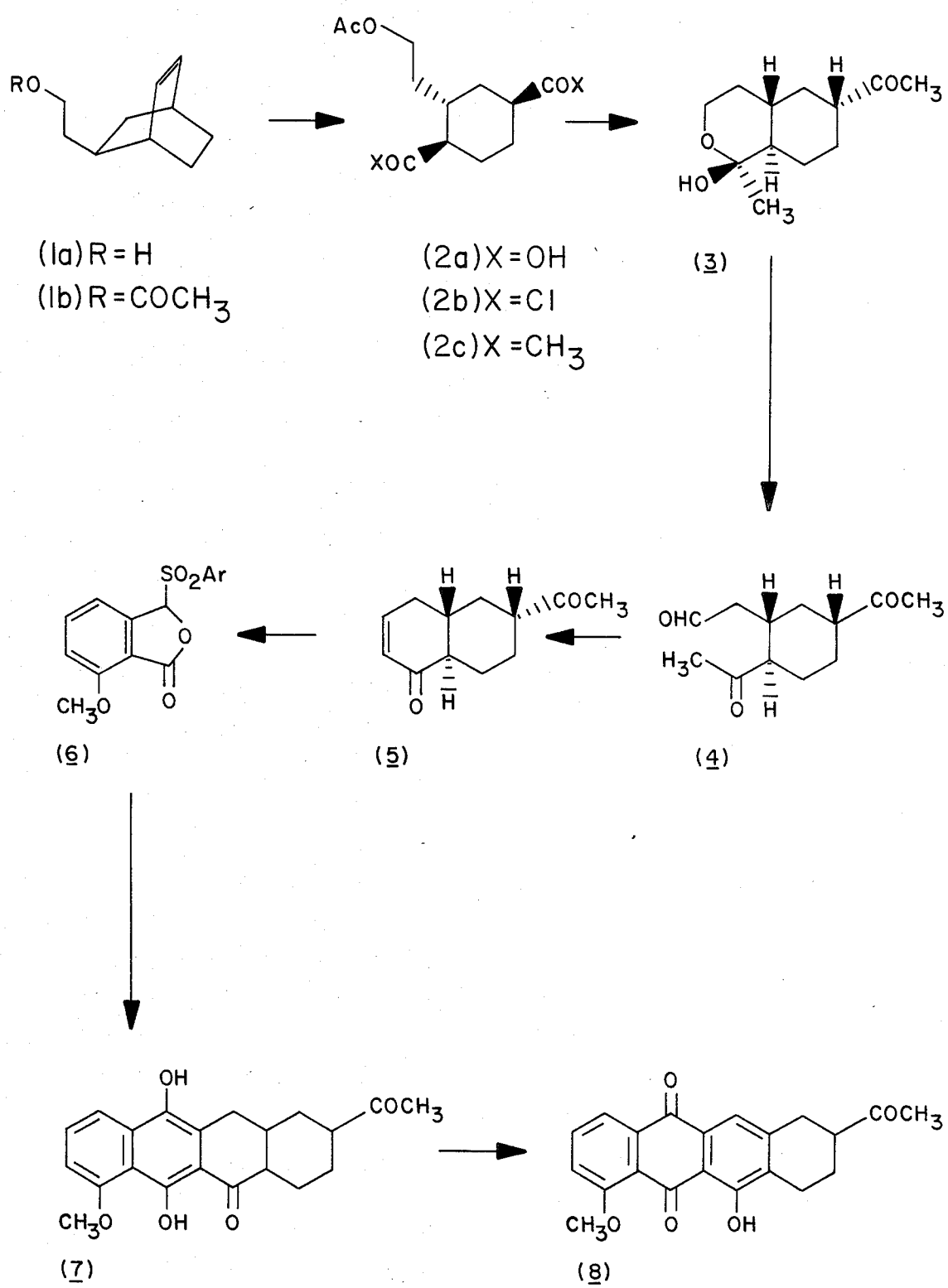

PRODUCTION OF A HEXAHYDRONAPHTHALENONE COMPOUND

CROSS-REFERENCE TO RELATED APPLICATION

This is a division of our prior-filed, co-pending patent application, Ser. No. 474,491, filed Mar. 11, 1983 now U.S. Pat. No. 4,481,143, for METHOD OF SYNTHESIZING A LATE-STAGE INTERMEDIATE TO 11-DEOXYDAUNORUBICIN AND 11-DEOXYADRIANMYCIN, AND TWO PRECURSORS TO THE OBJECT INTERMEDIATE.

BACKGROUND AND SUMMARY OF THE INVENTION

The work leading to the invention disclosed herein was generously supported by the National Cancer Institute (CA 18141) and by Career Development Award to Dr. Frank M. Hauser (CA 00487).

The present invention relates to the production (method and object compound thereof), from readily prepared starting materials, of 6-acetyl-4a,5,6,7,8,8a-hexahydro-1(4H)-naphthalenone, a novel compound which is especially useful as a precursor in the synthesis of 9-acetyl-6-hydroxy-4-methoxy-7,8,9,10-tetrahydronaphthacene-5,12-dione—an established late-stage intermediate to the anthracycline antibiotics 11-deoxydaunorubicin and 11-deoxyadriamycin.

The object hexahydronaphthalenone compound can be represented as:

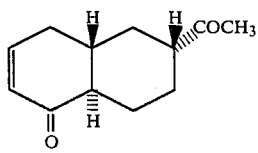

(5)

The anthracycline antibiotics 11-deoxydaunorubicin and 11-deoxyadriamycin, 11-deoxy analogs of the therapeutically useful anthracycline antibiotics daunorubicin and adriamycin, were isolated by Arcamone et al., J. Am. Chem. Soc. 1980, 102, 1462, from microorganisms. While these 11-deoxy compounds are somewhat less active as anticancer agents than either daunorubicin or adriamycin, they exhibit significantly less cardiotoxicity, and are potentially important compounds for the treatment of various cancers.

In view of the high cost of producing these antibiotics microbiologically, various attempts to develop effective synthetic routes for their production have been reported. Particular emphasis, for example, has been placed on preparing the aglycone fragment which can be coupled with daunosamine, the amino sugar fragment, to furnish the parent antibiotic. Syntheses of the aglycone have been reported by Sih et al., Tetrahedron Lett. 1980, 21, 3351; Rapoport et al., Tetrahedron Lett. 1980, 21, 4777; Mondon et al., Tetrahedron Lett. 1980, 21, 3351; J. Chem. Soc. Chem. Commun. 1982, 23, 421; Alexander et al., Tetrahedron Lett. 1981, 22, 3711; Rao et al., Tetrahedron Lett. 1982, 23, 775; and Johnson et al., J. Am. Chem. Soc. 1981, 103, 1561.

The reported procedures suffer from a number of disadvantages. Many are lengthy, low-yield sequences which utilize starting materials that are expensive and/or not readily available.

A general object of the present invention, accordingly, is to provide a convenient method for the preparation of 6-acetyl-4a,5,6,7,8,8a-hexahydro-1(4H)-naphthalenone which is a novel precursor compound to 9-acetyl-6-hydroxy-4-methoxy-7,8,9,10-tetrahydronaphthacene-5,12-dione, and in addition, to provide the novel precursor hexahydronaphthalenone compound itself.

Another and related object is to provide such a method which provides a relatively high overall objective-product yield.

Still another object of the invention is to provide a novel method which utilizes commercially available starting materials.

In accordance with a preferred manner of practicing the invention, the proposed method is characterized by conversion, in several convenient steps described in detail below, of 2-(2-hydroxyethyl)bicyclo[2.2.2]oct-5-ene to 6-acetyl-4a,5,6,7,8,8a-hexahydro-1(4H)-naphthalenone.

The method of the invention results in the production of the object hexahydronaphthalenone product in 55% overall yield.

Other objects and advantages of the invention will become apparent as the same is described below in conjunction with examples which specifically illustrate the invention and its utility. In the description which follows, identical compounds are identified by like numbers which are found in the schematic representations and in the description itself.

The novel synthesis of the object precursor, as well as an overall synthesis of the tetrahydronaphthacene dione (late-stage intermediate) which use the object precursor uniquely facilitates, are illustrated compactly on the single drawing page. Briefly outlining what is here shown, 2-(2-hydroxyethyl)-bicyclo[2.2.2]oct-5-ene (1a), the preparation of which has been described by Whitlock et al., J. Am. Chem. Soc. 1968, 90, 4929, and which is readily synthesized in six steps from commercially available, 1,3-cyclohexadiene and ethyl acrylate, served as the starting materials. Acetylation of (1a) with acetic anhydride furnished the acetate (1b). Cleavage of the olefinic entity is (1b), to give the cyclohexane dicarboxylic acid (2a), was accomplished in quantitative yield through oxidation with either ozone in acetic acid followed by subsequent workup with hydrogen peroxide, or through oxidation with a catalytic amount of in-situ-generated ruthenium tetroxide, using either sodium periodate or sodium hypochlorite as a co-oxidant. The dicarboxylic acid (2a) was converted to the diacid chloride (2b) through treatment with thionyl chloride in benzene containing a catalytic amount of triethylamine. Reaction of the acid chloride (2b) with methyl copper at −20° C. in ether furnished the acetoxydiketone (2b) as an intermediate, which was hydrolyzed with sodium hydroxide to give the lactol (3). (3) was conveniently purified through recrystallization. The overall yield of (3) from (2a) is routinely 44–46%. Oxidation of (3) with chromium trioxide in pyridine furnished 1,4-diacetyl-cyclohexane-2-acetaldehyde (4), which was not purified, but directly cyclized and dehydrated to give the object compound 6-acetyl-4a,5,6,7,8,8a-hexahydro-1(4H)-naphthalenone (5) in 55% yield. Purification of (5) was achieved through chromatography followed by recrystallization.

Continuing with a synthesis utilizing the object compound (5) to produce the tetrahydronaphthacene dione intermediate, the anion of 7-methoxy-3-phenylsulfonyl- 1(3H)-isobenzofuranone (6) as generated at −78° C. using lithium t-butoxide in THF and reacted with the hexahydronaphthalenone (5) to furnish 9-acetyl-5,12-dihydroxy-4-methoxy-6(11H)-hexahydronaphthacenone (7) in 95% yield. Conversion of (7) to 9-acetyl-6-hydroxy-4-methoxy-7,8,9,10-tetrahydronaphthacene-5,12-dione (8) was achieved by heating (7) in dimethylforamide under oxygen at 45° C. for 18 hours.

The tetrahydronaphthacene dione intermediate (8), prepared by the above-described procedure utilizing the object compound of the invention, can be employed conveniently in the production of both 11-deoxydaunorubicin, and 11-deoxyadriamycin, by first converting it to 7,9-dihydroxy-11-deoxydaunomycinone by the procedure of Johnson et al., J. Am. Chem. Soc. 1981, 103, 1561, and by then coupling this product with daunosamine, utilizing the procedure of Acton et al., J. Med. Chem. 1974, 17, 659–660.

The invention (method and compound) is further illustrated by way of the following detailed disclosure:

Preparation of 2-(2-acetoxyethyl)bicyclo[2.2.2]oct-5-ene (Compound 1b)

The bicyclo octenol (1a) (24.5 g, 161.0 mmol), which can be represented as follows:

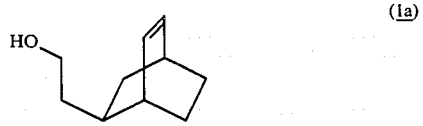

was prepared from commercially available cyclohexadiene and ethyl acrylate, utilizing procedures described by Whitlock et al., J. Am. Chem. Soc. 1968, 90, 4929, and Narazaki et al., J. Org. Chem. 1978, 43, 4745. (1a) was added to a mixture of acetic anhydride (35 mL) and pyridine (70 mL). The reaction was stirred at room temperature overnight, diluted with ether (200 mL), and poured into water (200 mL). The ether layer was separated and successively washed with water (100 mL), 10% hydrochloric acid (2×100 mL), and saturated sodium chloride (100 mL). The ether was evaporated and the residue distilled to give 31.0 g (99% yield) of (1b) as a colorless liquid. bp 70°–72° C. (0.5 mm); $^1$H NMR (CDCl$_3$) δ 6.40–6.0 (m, 2H), 4.03 (t, J=7.0 Hz, 2H), 2.60–2.18 (m, 2H), 2.03 (s, 3H), 1.84–0.70 (m, 9H); mass spectrum, m/z 194 (M+). Anal. Calcd. for C$_{12}$H$_{18}$O$_2$ (194.26): C, 74.19; H, 9.34. Found: C, 74.44; H, 9.30.

(1b) can be represented according to the following diagram:

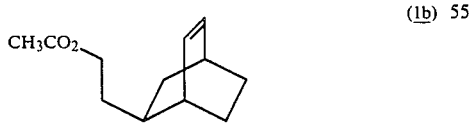

Preparation of 2-(2-acetoxyethyl)cyclohexane-1,4-dicarboxylic acid (Compound 2a)

To a solution of the acetate (1b) (4.8 g, 24.7 mmol) in acetone (120 mL) was added a solution of sodium metaperiodate (26.5 g, 123.5 mmol) in water (120 mL), followed by ruthenium trichloride hydrate (50 mg). The resulting mixture was stirred at room temperature overnight. Isopropanol (5 mL) was added, and the solids which were present were removed by filtration through a celite pad. The filtrate was concentrated under reduced pressure to half of its volume. Sodium bicarbonate (5 g) was added, and the water solution was washed with ether (100 mL) which was discarded. The aqueous solution was acidified with concentrated hydrochloric acid (10 mL), and extracted with ethyl acetate (3×200 mL). The combined ethyl acetate extracts were washed with brine (100 mL), dried using (MgSO$_4$), and concentrated under reduced pressure to give 6.0 g (93% yield) of the diacid (2a) as a viscous oil. $^1$H NMR (CDCl$_3$) δ 10.2 (brs, 2H), 4.15 (9t, J=7.0 Hz, 2H), 2.84–2.48 (m, 2H), 2.45–1.40 (m, 9H), 2.08 (s, 3H); mass spectrum, m/z 258 (M+). Sequential treatment of (2a) with base and acid gave the corresponding lactone with mp 165°–170° C. Anal. Calcd. for C$_{10}$H$_{14}$O$_4$ (198.21); C, 60.59; H, 7.12. Found: C, 60.54; H, 7.22.

(2a) may be represented as follows:

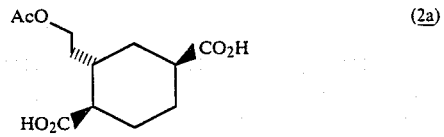

Preparation of 2-(3-acetoxyethyl)cyclohexane-1,4-dicarboxyl chloride (Compound 2b)

To a mixture of the diacid (2a) (6.0 g, 23.3 mmol) in anhydrous benzene (60 mL) was added thionyl chloride (10 mL) and triethylamine or pyridine (3 drops). The reaction was refluxed for 3 hours under a nitrogen atmosphere, then evaporated at reduced pressure to give 6.5 g (95.7% yield) of the diacid chloride (2b) as a brown oil. $^1$H NMR (CDCl$_3$) δ 4.40–3.95 (m, 2H), 3.40–1.40 (m, 11H), 2.08 (s, 3H); mass spectrum, m/z 295 (M+).

(2b) may be represented according to the following diagram:

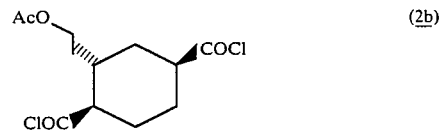

Preparation of 2-(2-acetoxyethyl)-1,4-bis(acetyl)cyclohexane (Compound 2c)

To a suspension of dry cuprous iodide (38.6 g, 200.0 mmol) in anhydrous ether (900 mL) at −40° C. under a nitrogen atmosphere was added, with stirring, a solution of methyllithium (143 mL of 1.4M, 200 mmol). The ether solution of methyl copper was stirred for 15 minutes, at which time the acid chloride (2b) (13.4 g, 45 mmol) was slowly added. The reaction mixture was allowed to come to ambient temperature, then quenched with saturated ammonium chloride solution (400 mL). The ether layer was separated, and the aqueous layer was extracted with ether (200 mL). The organic phases were combined, dried using (MgSO$_4$), and concentrated to give 8.5 g (74%) of diketone (2c) as a yellowish oil which was used in the next step without further purification. ¹H NMR δ 4.09 (t, J=6 Hz, 2H), 3.0-2.64 (m, 2H), 2.14 (s, 3H), 2.13 (s, 3H), 2.04 (s, 3H), 2.0-1.2 (m, 9H); mass spectrum, m/z 254 (M+).

(2c) can be represented by the following:

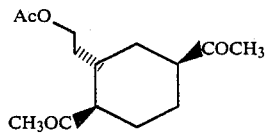

(2c)

Preparation of 6-acetyl-1-hydroxy-1-methyl-3,4,4a,5,6,7,8,8a-octahydro-1H-2-benzopyran (Compound 3)

To a solution of (2c) (8.5 g, 33.5 mmol) in methanol (60 mL) was slowly added a solution of sodium hydroxide (4.0 g) in water (60 mL). The resulting mixture was stirred at ambient temperature for 1 hour, then evaporated at reduced pressure to remove most of the methanol. The basic aqueous solution was extracted with ether (4×200 mL), and the combined ether extracts were washed with brine (50 mL), then dried using (MgSO₄), and concentrated at reduced pressure to give (3)—a pale yellow solid. Recrystallization of this material from ethylacetatehexane furnished 4.2 g (59.1% yield) of alcohol (3): mp 115°-116° C., ¹H NMR (CDCl₃) δ 4.16-3.50 (m, 3H), 2.60-2.20 (m, 1H), 2.14 (s, 3H), 2.0-1.8 (m, 10H), 1.39 (s, 3H); mass spectrum, m/z 212 (M+). Anal Calcd. for $C_{12}H_{20}O_3$ (212.28): C, 67.89; H, 9.50. Found: C, 67.70; H, 9.50.

Compound (3) can be visualized according to the following diagram:

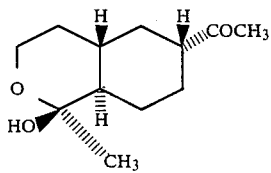

(3)

Preparation of 6-acetyl-4a,5,6,7,8,8a-hexahydro-1(4H)-naphthalenone (the object compound 5)

To a well stirred suspension of pyridinium chlorochromate (14.8 g, 68.5 mmol) in anhydrous methylene chloride (130 mL) was added a solution of alcohol (3) (2.9 g, 13.7 mmol) in anhydrous methylene chloride (20 mL). The resulting mixture was stirred at room temperature overnight, at which time the methylene chloride was decanted from the solids that were present. The solid residue was washed with ether, and the ether washing was combined with the methylene chloride, then dried using (MgSO₄), filtered and evaporated at reduced pressure to furnish 2.1 g (73% yield) of 2-(2,5-diacetylcyclohexane-acetaldehyde (4). ¹H NMR (CDCl₃) δ 10.32 (brs, 1H), 2.64-1.80 (m, 11H), 2.16 (s, 6H); mass spectrum, m/z 210 (M+).

(4) may be represented schematically as follows:

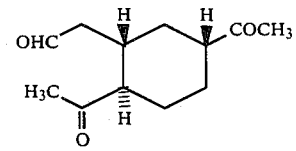

(4)

The acetaldehyde intermediate (4) (2.1 g, 10 mmol) was taken up in tetrahydrofuran (200 mL), and water (0.5 mL) and concentrated hydrochloric acid (1.0 mL) were added. The solution was heated at reflux for 5 hours, then diluted with water (20 mL) and evaporated at reduced pressure to remove most of the tetrahydrofuran. The residual aqueous solution was extracted with ether (3×200 mL), and the combined ether extracts were successively washed with saturated sodium bicarbonate solution (20 mL), brine (50 mL), then dried and concentrated to give a semisolid. Recrystallization from benzene hexane provided 1.0 g (52.1%) of the object compound (5). mp 86°-91° C., ¹H NMR (CDCl₃) δ 7.04-6.78 (m, 1H), 6.12-5.84 (m, 1H), 2.60-1.0 (m, 11H), 2.16 (s, 3H); mass spectrum, m/z 192 (M+).

(5) can be represented according to the following diagram:

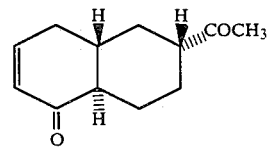

(5)

Utilization of this object compound (5) in a synthesis to produce the tetrahydronaphthacene dione intermediate to the named anthracycline antibiotics is described by the following steps:

Preparation of 9-acetyl-5,12-dihydroxy-4-methoxy-6(11)-hexahydronaphthacenone (Compound 7)

To a magnetically stirred solution of lithium t-butoxide (8.8 mmol, prepared from 8.8 mmol of n-BuLi and 9.0 mmol of t-BuOH in 100 mL of THF), cooled to −78° C., was slowly added a slurry of 7-methoxy-3-phenylsulfonyl-1(3H)-isobenzofuranone (6) (0.91 g, 3 mmol), in THF (20 mL).

(6) may be represented as follows:

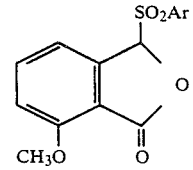

(6)

After stirring the resulting solution for 5 minutes, (5) (0.9 g, 4.7 mmol) was added and the reaction mixture was stirred at the same temperature (−78° C.) for 10 minutes. The cooling bath was removed, and the reaction mixture was stirred at the ambient temperature for 1 hour, then acidified with 2 mL of 6N HCl, whereupon bright yellow crystals of (7) precipitated out. The crystals were collected by filtration and washed with CH₂Cl₂ (50 mL) to furnish 0.98 g (92.5% yield) of pure 9-acetyl-5,12-dihydroxy-4-methoxy-6(11H)-hexahydronaphthacenone (7). mp 223°-226° C.; mass spectrum, m/z 354 (M+). Compound (7) was found to be extremely sensitive to air oxidation, and satisfactory combustion analyses could not be obtained. The observation that (7) was air sensitive was utilized to oxidize it to (8).

(7) can be represented as follows:

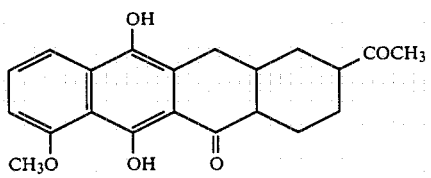
(7)

Preparation of 9-acetyl-6-hydroxy-4-methoxy-7,8,9,10-tetrahydronaphthacene-5,12-dione (Compound 8)

A solution of (7) (0.4 g, 1.1 mmol) in dimethylformamide (40 mL) was heated at 110° C. Simultaneously, oxygen was bubbled through it. After 2 hours, flow of oxygen was terminated and 2 mL of water was added. Upon cooling, the reaction mixture gave orange crystals of (8).

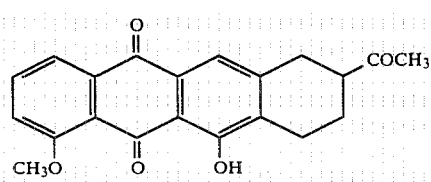
(8)

These crystals were collected by filtration, washed with water and dried: yield 0.37 g (94% yield) of (8) with mp 222°–225° C. (lit. mp 223°–226° C.), $^1$H NMR (CDCl$_3$) δ 13.36 (s, 1H), 8.08–7.22 (m, 4H), 4.07 (s, 3H), 3.30–2.40 (m, 4H), 2.27 (s, 3H), 2.27 (m, 1H), 2.0–1.4 (m, 2H), mass spectrum, m/z 350 (M+). Anal. Calcd. for C$_{21}$H$_{18}$O$_5$ (350.35): C, 71.99; H, 5.18. Found: C, 71.70; H, 5.30.

It is claimed and desired to secure by Letters Patent:

1. The compound having the formula

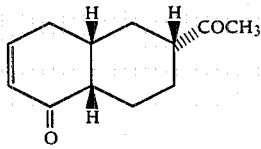

2. A method for synthesizing the compound having the formula

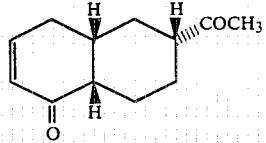

which comprises
acetylizing 2-(2-hydroxyethyl)bicyclo[2.2.2]oct-5-ene to furnish 2-(2-acetoxyethyl)bicyclo[2.2.2]oct-5-ene,
cleaving the olefinic entity in the latter acetate to give 2-(2-acetoxyethyl)cyclohexane-1,4-dicarboxylic acid,
converting the dicarboxylic acid to the diacid chloride 2-(3-acetoxyethyl)cyclohexane-1,4-dicarboxyl chloride,
reacting the dicarboxyl chloride with methyl copper to furnish the acetoxydiketone 2-(2-acetoxyethyl)-1,4-bis(acetyl)-cyclohexane,
hydrolyzing the the acetoxydiketone with sodium hydroxide to give the lactol 6-acetyl-1-hydroxy-1-methyl-3,4,4a,5,6,7,8,8a-octahydro-1H-2-benzopyran,
oxidizing the lactol to produce 1,4-diacetyl-cyclohexane-2-acetaldehyde, and
cyclizing and dehydrating the latter to yield the object compound.

* * * * *